United States Patent [19]
Scholl

[11] Patent Number: 6,126,880
[45] Date of Patent: Oct. 3, 2000

[54] PRODUCTION OF A PROPHYLACTIC

[75] Inventor: Thomas Scholl, Munich, Germany

[73] Assignee: Innovation & Art GmbH, Munich, Germany

[21] Appl. No.: 08/894,348

[22] PCT Filed: Dec. 15, 1996

[86] PCT No.: PCT/DE96/02405

§ 371 Date: Sep. 30, 1997

§ 102(e) Date: Sep. 30, 1997

[87] PCT Pub. No.: WO97/22454

PCT Pub. Date: Jun. 26, 1997

[30] Foreign Application Priority Data

Dec. 15, 1995 [DE] Germany ............... 195 46 985

[51] Int. Cl.$^7$ ............... B28B 7/04; B28B 1/38
[52] U.S. Cl. ............... 264/219; 264/301; 264/303; 264/304; 264/305; 425/274; 425/275; 425/436 RM; 451/41; 451/56; 451/177; 451/259
[58] Field of Search ............... 264/219, 301, 264/303, 305, 334, 335, 304; 425/270, 269, 272, 274, 275, 404, 469, 436 RM; 451/41, 56, 177, 259

[56] References Cited

U.S. PATENT DOCUMENTS

| | | | |
|---|---|---|---|
| 1,923,733 | 8/1933 | Killian | 425/274 |
| 2,021,299 | 11/1935 | Gammeter | 264/301 |
| 2,968,134 | 1/1961 | Lewis | 51/124 |
| 4,903,679 | 2/1990 | Kiger et al. | 125/11 R |
| 5,323,544 | 6/1994 | Osgood | 34/247 |
| 5,409,416 | 4/1995 | Eichhorn et al. | 451/41 |

FOREIGN PATENT DOCUMENTS

| | | |
|---|---|---|
| 123532 | 2/1931 | Austria . |
| 4409449 | 8/1995 | Germany . |
| 96564 | 10/1922 | Switzerland . |
| 1142433 | 2/1969 | United Kingdom . |

*Primary Examiner*—Catherine Timm
*Assistant Examiner*—Suzanne E. Mason
*Attorney, Agent, or Firm*—Collard & Roe, P.C.

[57] ABSTRACT

A plunger tool for producing a special prophylactic is disclosed. The special features of the plunger tool reside in the special curvatures in its shaped section. The shaped section of the plunger tool exhibits an extreme narrowing, at the deepest point of which there may be at least one annular groove. Unlike prior art transitions, the transition from the large diameter to the reservoir section is not steep and straight but takes the form of an S-shaped curve. An exact contour of the annular grooves on the surface of the plunger tool is essential for their production and can be done only by the use of a precision diamond abrasive point.

16 Claims, 8 Drawing Sheets

PRODUCTION OF A PROPHYLACTIC

The present invention relates to the production of a shaped prophylactic with special roundings, in connection with which the special form of a plunger tool, on the one hand, and the manufacturing process, on the other hand, play important roles.

Such a plunger tool and process for the manufacture of a prophylactic have been introduced and described in detail in international application 95/25622, or DE 4409449 C1. A prophylactic consisting of an oblong, cylindrical shaft with an end closed by an S-shaped section, and a reservoir section adjoining the latter, is manufactured with said known plunger tool. Provision is made for a deepening which, when the prophylactic is used, comes to rest within the zone of the glans, such deepening being formed by two blunt cones abutting each other with their covering surfaces. The deepening has an opening angle in the range between 60° and 120°. The known prophylactic is produced by immersing it three times in a latex solution. Between each immersing operation, it is passed through a drying furnace, and at the end of the last immersing operation, the known prophylactic is stripped off by means of brushes rotating in opposite directions.

Furthermore, similar processes and devices for producing thin-walled shaped bodies particularly made of natural rubber compounds are well-known in the state of the art. With the known methods for producing a prophylactic, the plunger tool is undergoing three immersion steps when provided with difficult shapes. The three immersion steps are especially important with shapes having relatively small radii of curvature in certain sites of the plunger tool, so that the elastic material (latex) to be applied on such small radii of curvature is distributed unevenly, which is frequently the cause for tearing and breaking spots, so that the prophylactic fails to satisfy the requirements of the testing authorities.

Since it is generally difficult to manufacture a prophylactic that satisfies the high application requirements with respect to good fit and easy handling, various shapes have been proposed in the state of the art particularly for the upper part of the prophylactic, such shapes being expected to solve the problems on hand. This includes UK-PS 1,142,443, which is known in the state of the art from the year 1967. A prophylactic is known from said patent which has a cylindrical part and an upper shaped part. The upper shaped part of said known prophylactic has a narrowing, which is shaped in such a way that it is expected to assure, a safe fit on the erected male organ. Said prophylactic, however, has no reservoir part at the top end of the prophylactic, as it now can be found on each commercially available prophylactic. Such prophylactics are no longer permissible if only for said reason.

Another decisive drawback is that the radius of curvature of the constriction of the prophylactic in the upper part uniformly extends through the entire deepening, which means that adequately good adaptation to the anatomical conditions of the male penis is not assured at all.

Furthermore, a condom made of rubber became known in 1929 from Austrian patent specification No. 123 532. Said condom has a constriction (a) in the top shaped part and consists of two blunt cones abutting each other with their covering surfaces, whereby the contact points of the blunt cones are smooth. However, the shapes of the plunger tools shown in said patent specification have highly pronounced S-curves of the jacket surfaces of the blunt cones, so that the realization of such a prophylactic for practical use is problematic.

A short condom with a club-like reservoir part is known from CH 96564, which has to be glued to the penis of the user. No measures are disclosed in CH 96564 that would indicate that the club-like reservoir part is raised into an upright position of use by pressure and tensile stresses caused by any special shaping.

The objective of the present invention is to protect a novel type of prophylactic with pronounced shapes in the upper part, whereby the radii of curvature of the individual roundings play a decisive part in the predetermined sites, such radii having a decisive bearing on the inner pressure and tensile stresses or the prophylactic both in the rolled-up and unrolled condition of the latter.

Therefore, the problem of the present invention is to make available a prophylactic assuring optimal fit and safe handling.

Said problem is solved according to the invention by the features specified in claims 1, 2 and 8.

The plunger tool according to the invention for producing a prophylactic is characterized in that the diameter (D5) of the plunger tool (1) at the deepest point of the narrowing (6) amounts to between 15 and 25 mm;

the radius of curvature (R1) at the narrowest point (D5) of the narrowing (6) amounts to between 17 and 20 mm;

the openings angle of the upper blunt cone (9), the latter being open toward the reservoir part (4), amounts to 50%;

the opening angle of the lower blunt cone (8) amounts to 40%;

the radius of curvature at the point of transition from the cylindrical section (2) to the narrowing (6) in the shaped section (3) is convex and greater than 25 mm;

the total length from the narrowing (6) to the inlet in the reservoir part (4) amounts to between 45 mm and 65 mm; and the greatest diameter (D2) of the shaped section (3) within the zone between the narrowing (6) and the inlet zone leading into reservoir part (4) amounts to between 33 and 35 mm.

In this connection, the smallest radius of curvature, i.e., the strongest curvature of the narrowing is found in about the center of the narrowing. Weakly shaped S-curves extend from said curvature toward both sides, said S-curves representing the jacket surfaces of two blunt cones abutting each other with their small covering surfaces.

Another embodiment according to the invention is characterized in that the narrowing has near the narrowest diameter (D5) at least one annular groove, so that at least one ring is formed in this way on the finished prophylactic, such ring having a mass very much greater than the mass of the elastic material within its environment. Advantageous for the prophylactic of the invention are two such annular grooves, which are spaced from each other by about 1.5 mm.

Particularly advantageous for the Prophylactic according to the invention is the so-called reservoir section (4) arranged on the top end, which, according to the invention, is designed in the way of a club. Owing to the special roundings and dimensional conditions of the reservoir section according to the invention, the latter has the property that it is standing upright in the direction of use after it has been pulled from the sales packaging. Such erection of the reservoir section in the rolled-up condition of the prophylactic is possible only if tensile and pressure stresses are caused within the prophylactic due to its shaping in the shaped section of the prophylactic, such stresses being directed in such a way that the reservoir section is standing in the direction of use with its center axis perpendicular to the plane of the rolled-up prophylactic.

In addition, the special shaping with its smooth roundings offers the advantage that the elastic material gets evenly distributed over the plunger tool when it is immersed in the individual immersion basins, so that the prophylactic has no thin spots at all, which frequently are the cause of defects of the prophylactic.

Furthermore, it is advantageous and in accordance with the invention that the transition from the greatest diameter of the plunger tool in the shaped section to the reservoir section is not steep and straight, but represents a downwardly slanted, swung S-curve.

Owing to the shaping of the plunger tool according to the invention, it is possible to make available a process according to the invention For producing the prophylactic, in which the plunger tool is immersed in two immersion steps in the elastic material (latex) to be applied, rotating around its longitudinal axis at a certain angle relative to the surface. Provision is made for a drying step in a special drying furnace following each immersion step.

Another aspect according to the invention in the process of the invention for producing the prophylactic is that the plunger tool is provided on the surface with annular grooves ground into the surface with the help of at least one disk-like, finely granular diamond cutting point, with their angles (alpha) being between 60° and 120°, whereby the front part of the diamond cutter tip has a blunted section, which is especially required so that the annular groove to be cut on the surface of the plunger tool will not have any sharp edges, on which elastic material could stick in the immersion steps, which would require special cleaning operations.

According to one embodiment, the annular grooves extent symmatrically relative to their center axis.

According to another variation of te annular grooves cut according to the invention, such annular grooves are shaped asymmetrically relative to the center axis in such a way that the wall of the annular groove to the left of the axis (in FIG. 11) extends steeper than the wall to the right of the axis. An important aspect in the asymmetry of the annular groove is to be seen in that the ratio of the spacings (A, A') relative to the center axis of the annular groove amounts to about 1:2. This assures favorable spreading of the latex or some other elastic material to be applied In general, stripping of the finished prophylactic from the plunger tool presents a problem with prominent shapes. According to the invention, this problem is solved in that during the stripping operation, at least one water jet is directed by special brushes rotating in opposite directions in such a way that such jet acts upon the plunger tool during the stripping operation behind the rolled ring formed by the brushes. An extremely thin film of water is produced in this way between the finished prophylactic and the plunger tool, permitting stripping of the finished prophylactic, to begin with.

Additional features according to the invention are contained in the dependent claims.

The present invention is explained in greater detail in the following by reference to the drawings, in which.

Figure 1:
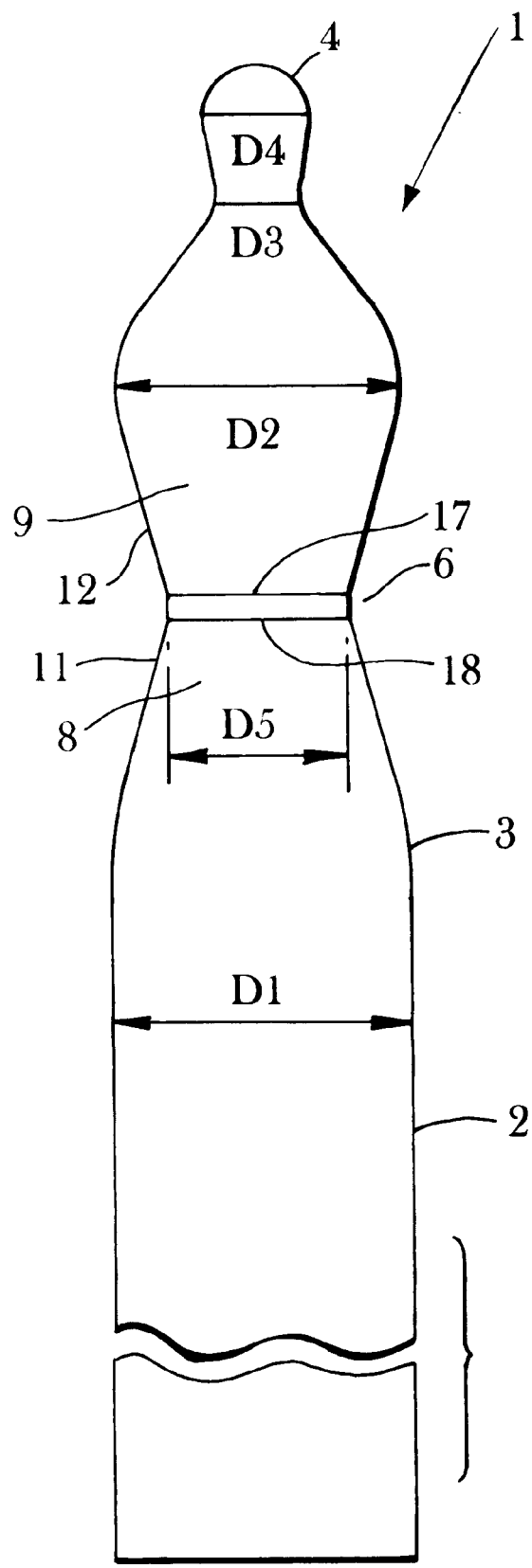
FIG. 1 shows a schematic view of a plunger tool (1) according to the invention by a lateral representation reflecting the basic shape of the upper part (3) of the plunger tool (1)

In FIG. 1, the plunger tool 1 is shown by a lateral schematic view. With the present exemplified embodiment, the plunger tool is made of glass. But the plunger tool can be made of other materials such as porcelain, plastic, ceramic materials or the like as well. Plunger tool 1 substantially consists of a long-stretched cylindrical part 2 and an upper shaped section 3. Diameter D1 of cylindrical part 2 amounts to about 34 mm. The long-stretched lower cylindrical part 2 is adjoined by the upper shaped section 3, joining the former seamless without any noticeable transition. The transition from the cylindrical section to the shaped section has a relatively large radius of curvature. The upper shaped section 3 of plunger tool 1 is in turn composed of three main components, which include two blunt cone-like structures 8 and 9 having jacket surfaces describing a swung S-curve. The two blunt cone-like structures 8 and 9 abut each other with their small contact surfaces seamlessly. At the point of abutment, narrowing 6 according to the invention has its deepest point and thus its narrowest diameter D5 as well. Diameter D2 of blunt cone 9 is nearly the same as diameter D1 of the long-stretched cylindrical section 2 of plunger tool 1. The radius of curvature of narrowing 6 is the smallest at the points of abutment of blunt cones 8 and 9 and, therefore, has the strongest curvature in said points, as compared to the curvatures of jacket surfaces 11, 12 of blunt cones 8, 9. The transition to the so-called reservoir section 4 practically starts from diameter D2 of blunt cone 9. The transition is described in greater detail further below because it is important. Diameter D3 of the inlet of the reservoir section is slightly smaller than diameter D4 in the upper zone of reservoir section 4.

According to another embodiment of plunger tool 1 of the invention, said plunger tool may have at least one annular groove or ring near the deepest point of narrowing 4. In the present case, two annular grooves 17, 18 are present in narrowing 6. The spacing between annular grooves 17 and 18 comes to approximately 1.5 mm.

Figure 2:
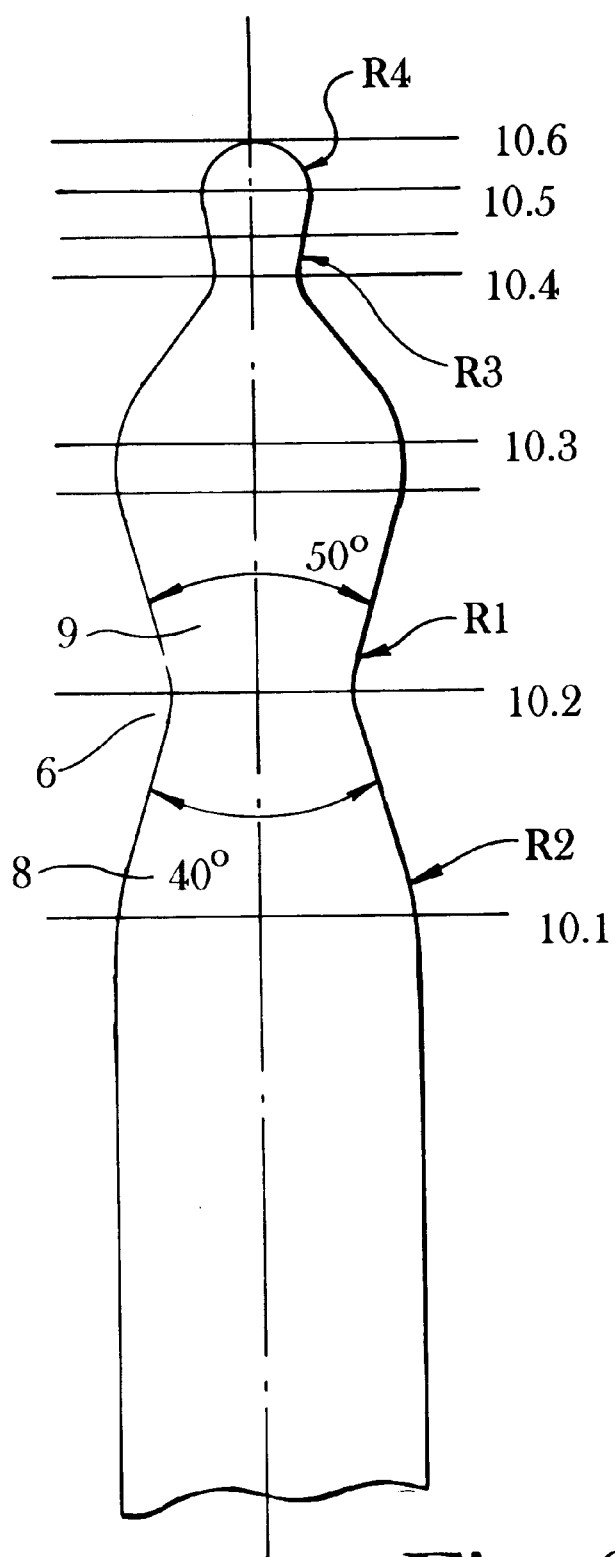
FIG. 2 shows a schematic representation of the plunger tool (1) seen by a lateral view with different planes of dimension (10), the latter being important for the dimensioning of the plunger tool (1)

FIG. 2 shows a schematic lateral view of another plunger tool 1 according to the invention, shown with the different dimensional planes 10.1 to 10.6. Dimensionial planes 10 are imaginary lines, which are required for dimensioning plunger tool 1 with the pre(sent exemplified embodiment. Dimensional plane 10.2 extends congruently parallel with diameter D5 of the narrowest point of narrowing 6. The ideal measure of diameter D5=20 mm; however, it may vary between 15 and 25 mm. Dimensional plane 10.3 extends through diameter D2, which comes to about 34 mm. Dimensional plane 10.4 extends through diameter D3, which amounts to about 10 mm, and dimensional plane 10.5 extends through diameter D4=12 mm. Dimensional plane 10.6 represents the end of plunger tool 1, which corresponds with the end of reservoir section 4. An advantageous measure for the total length pf shaped section 3 of plunger tool 1 amounts to about 100 mm and extends from dimensional plane 10.1 to dimensional plane 10.6. The measure for the spacing of dimensional plane 10.1 from dimensional plane 10.2 amounts to about 33 mm, and the measure for the spacing of dimensional plane 10.2 from dimensional plane 10.4 cones to about 50 mm. The measure for the spacing of dimensional planet 10.4 from dimensional plane 10.6 amounts to about 16 mm.

The opening angles of the blunt cones vary, whereby the lower blunt cone 8 has an opening angle of 40° and the upper opening angle of blunt cone 9 amounts to 50°. Radius of curvature R1 comes to 18 mm in the present case, whereby radius of curvature R2 is $\geq 25$ mm. Radius of curvature R3 at the foot of reservoir section 4 comes to 12 mm near diameter D3. Radius of curvature R4 at the upper end of reservoir section 4 comes to 6.5 mm. The total length of the reservoir section from dimensional plane 10.4 to dimensional plane 10.6 amounts to 16 mm.

Figure 3:
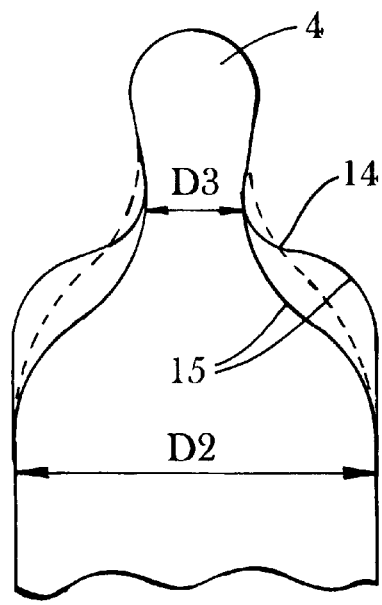
FIG. 3 represents a basic diagram of the reservoir section (4) of the plunger tool (1) with its special shape of the transition (15) from the large diameter (D2) to the reservoir section (4)

FIG. 3 shows the uppermost part of plunger tool 1, i.e., reservoir section 4 with the important transitions from diameter D2 to the lower diameter D3 of the lower part of reservoir section 4. It is important in this connection and in accordance with the invention that both the club-like reservoir section 4 and transition 15 have special shapes, which may not be steep as indicated by dashed line 14 as with the state of the art, but which has to describe a swung S-shaped line, which finally produces the stresses in the finished, rolled-up prophylactic and causes reservoir section 4 to stand upright relative to the plane of the rolled-up prophylactic.

Figure 4:
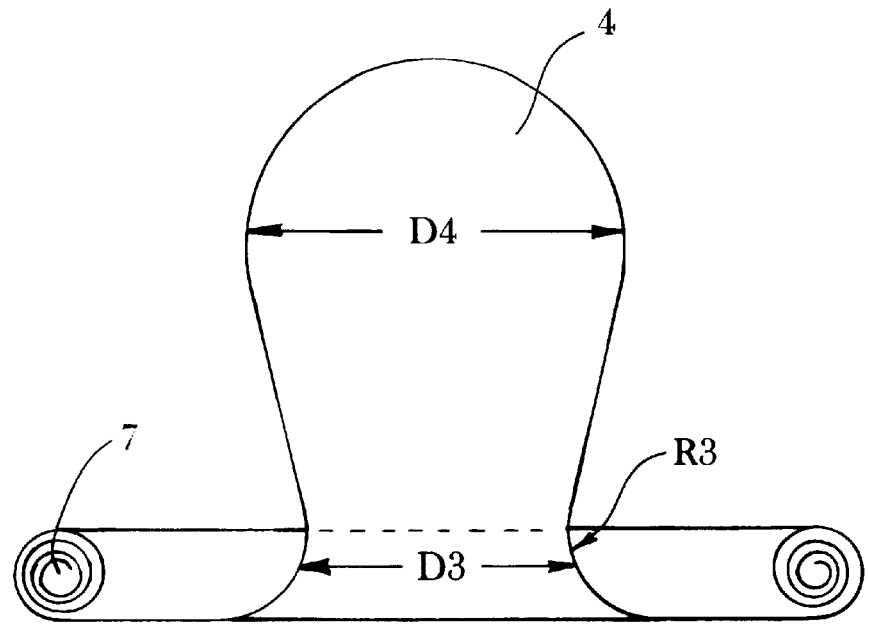
FIG. 4 shows a basic diagram of the rolled-up prophylactic with the reservoir section (4) standing upright in the direction of use.

A rolled-up prophylactic is schematically shown in FIG. 4. Due to the special shape of transition 15 and of the radii of curvature R3 near diameter D3 of reservoir section 4, stresses are produced here due to the pretension caused by the rolled ring 7 of the rolled-up prophylactic, such stresses being directed in such a way that reservoir section 4 stands upright in the direction of use after the prophylactic has been unpacked.

Figure 5:
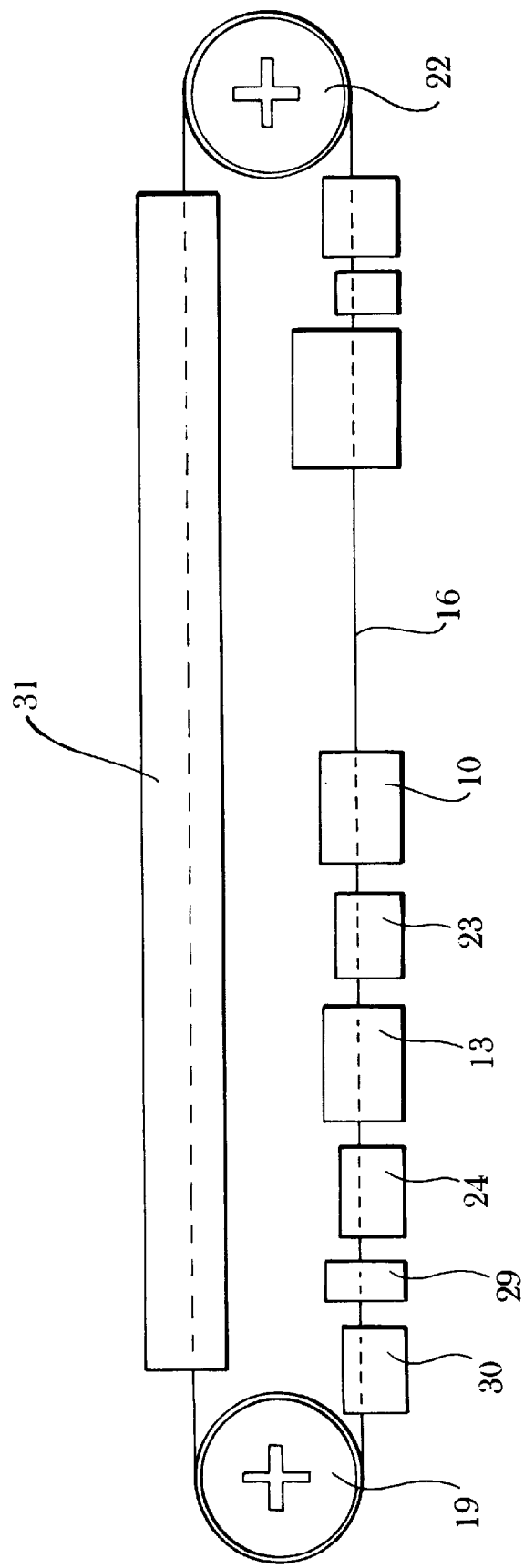
FIG. 5 shows a basic diagram of the immersing and drying device according to the invention for producing a prophylactic.

A device for the mass production of a prophylactic is schematically shown in FIG. 5. The total length of this plant installation from one reversing wheel 19 to the other reversing wheel 22 amounts to about 30 meters. Plunger tool 1 is secured on an endless conveyor belt 16 by a mechanism not to be described in greater detail, so that plunger tool 1 passes through the individual process stages at a defined rate. Said process stages are described in greater detail in the aforementioned published reference WO 95/25622. It is important in connection with the process according to the invention that in the present case, only two immersion operations are carried out in immersion basins 10 and 13. After plunger tool 1 was rotatingly passed through immersion basin 10, a first drying step takes place in device 23, through which plunger tool 1 is passing, rotating in the horizontal position. Following the second immersion stage in basin 13 and the second drying device, a rolling edge 7 is formed in device 29 with the help of brushes (not shown) rotating in opposite directions, such edge being formed on the open part of the prophylactic. Thereafter, the almost finished prophylactic is subjected to intermediate drying in device 30. Vulcanizing line 31 is a long-stretched furnace extending almost over the entire length of the installation.

Figure 6:
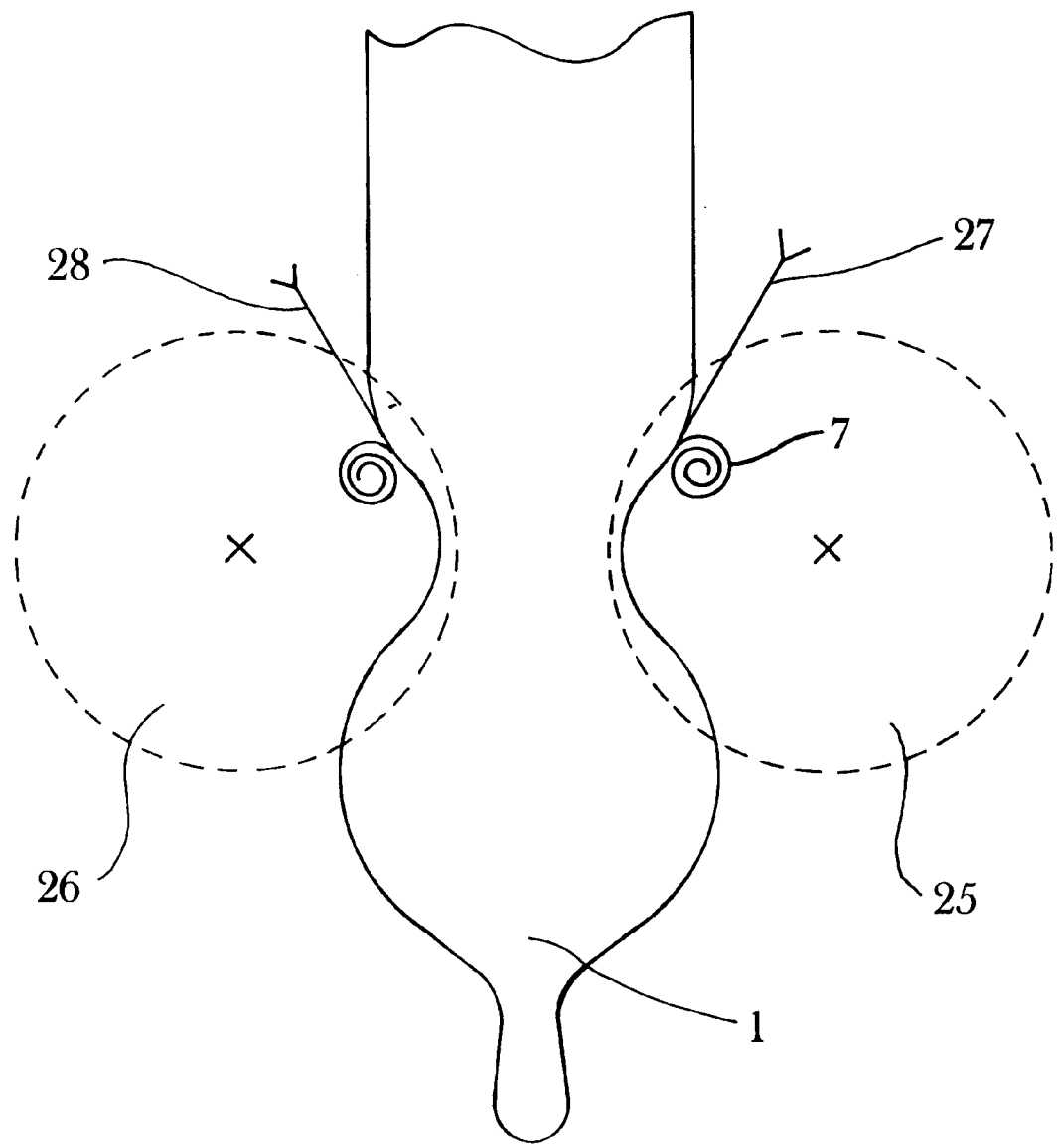
FIG. 6 shows a schematic view of the stripping device with the water jets (27, 28) according to the invention, such jets acting on the plunger tool (1) behind the brushed-off prophylactic.

FIG. 6 basically shows the stripping device for stripping the finished prophylactic from plunger tool 1. Two brushes 25, 26 rotating in opposite directions act on plunger tool 1, stripping the prophylactic from the tool. Due to the extremely small diameter D5 at the narrowest point of narrowing 6, it is difficult to strip the finished prophylactic from plunger tool 1 only with the help of brushes 25, 26. This problem is solved in that at least one water jet 27, 28 acts on plunger tool 1 behind the formed rolling ring 7 in such a way that a light film of water is formed between the prophylactic and the plunger tool, which permits stripping off the prophylactic. Water jet 27, 28 may act on the plunger tool in a cycled way or continuously depending on the requirements.

Figure 7:
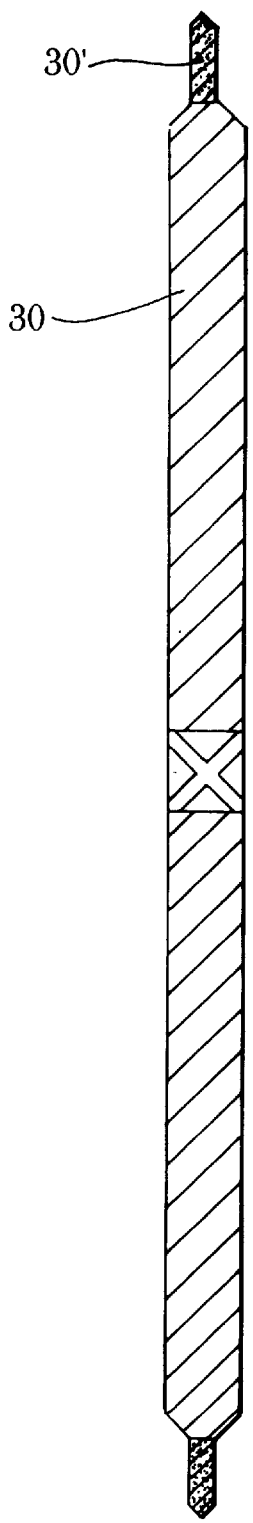
FIG. 7 shows a cross section through the grinding disk (30) with the diamond grinding tips (31, 32) according to the invention.
Figure 8:
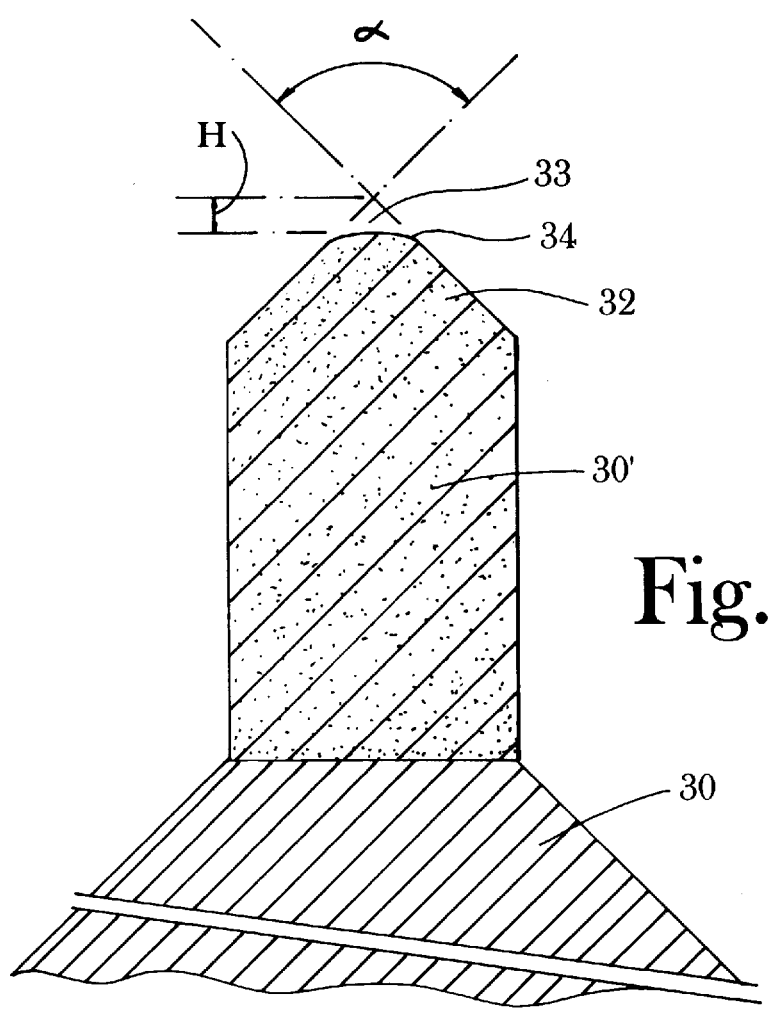
FIG. 8 shows an enlarged view of the diamond grinding tips (31, 32) according to the invention.

FIG. 7 shows a schematic view of the cross section of a round grinding wheel 30 having a sintered diamond attachment 30' applied to its periphery. Carrier wheel 30 has a thickness of about 10 mm and a diameter of approximately 200 mm. The material of the carrier wheel may be a hardened, reinforced epoxide resin; however, other suitable materials can be used as well. Sintered diamond attachment 30' with the diamond grinding tip 32 according to the invention is mounted on the periphery of carrier wheel 30 along the circumference. At the end, diamond attachment 30' has a tip having a defined angle (alpha), which is shown in FIG. 8 on an enlarged scale. Angle alpha is generally to be selected in the range of 60° and 120° depending on which type of annular groove is heeded. The most frequently used angle is alpha=90°. So as to provide annular (groove 17, 18 on the surface of plunger tool 1 with an appropriate cross section shape, top part 33 of diamond grinding tip 32 is slightly blunt, so that the edges 34 of the grinding tip are round. Height (H) of blunted section 33 advantageously comes to between 0.2 and 0.6 mm and is selected depending on the application case. It is important in this connection that a certain radius of curvature—in the present case r=0.4 mm—is present on the edges.

Figure 9:
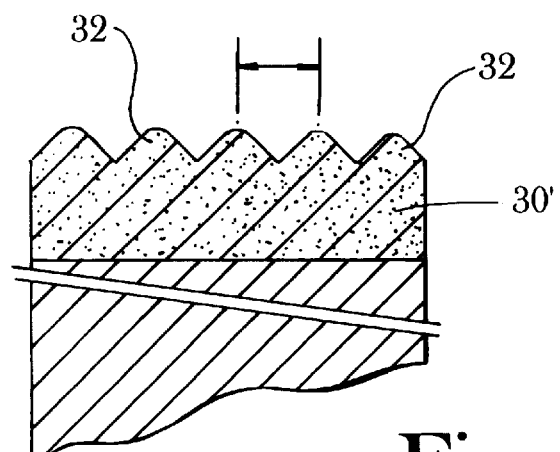
FIG. 9 shows an enlarged view of a diamond grinding tip (31) with five equal grinding points (32) according to the invention.

FIG. 9 shows another exemplified embodiment of diamond attachment 30' shown by a cross sectional view. In case a great number of annular grooves 17, 18 have to be ground one next to the other, it is useful to arrange several diamond grinding tips 32 on an attachment 30'. Thus five annular grooves 17 could be produced with such an attachment in one grinding operation. The production time for producing the annular grooves 17, 18 is reduced in this way multiple times.

The graininess of grinding tips 32 has to be relatively fine so that no furrows are drawn into the annular groove, where the elastic material would trapped. Typical granulations are, for example D10, D20 to D60.

Figure 10A:
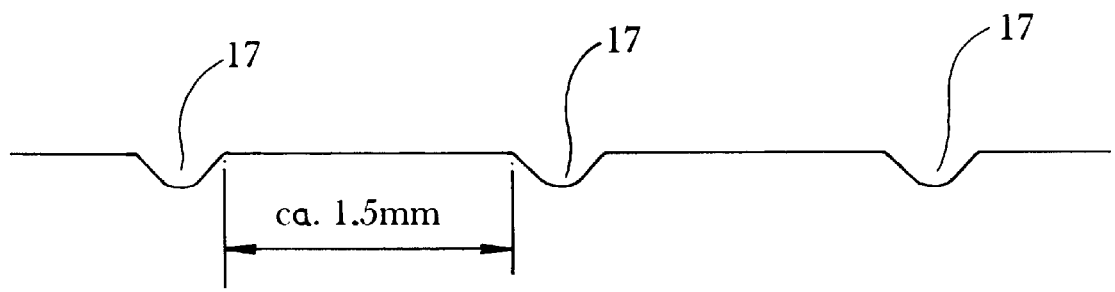
FIG. 10a shows a symbolized arrangement of symmetrical annular grooves (17, 18) on the surface of the plunger tool (1)
Figure 10B:
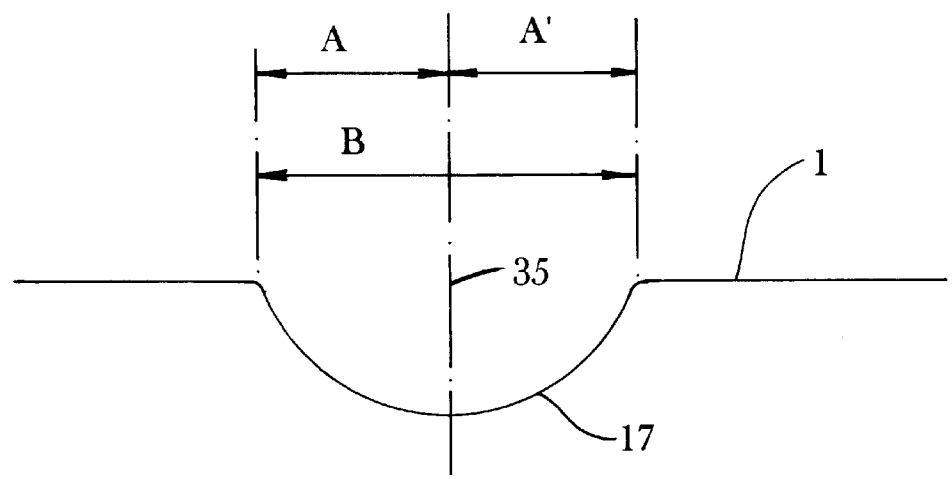
FIG. 10b shows an enlarged, symmetrical annular groove (17, 18)

FIG. 10a shows a cutout of the surface of a plunger tool 1 having symmetrical annular grooves 17 ground into it with the diamond grinding tips 32 according to the invention. The typical widths (B) of the openings of the symmetrical annular grooves 17 are between 0.3 mm to 0.6 mm (see FIG. 10b). The spacings between the individual annular grooves 17 can be freely selected; however, such spacings should not significantly fall short of 1.5 mm.

Figure 11A:
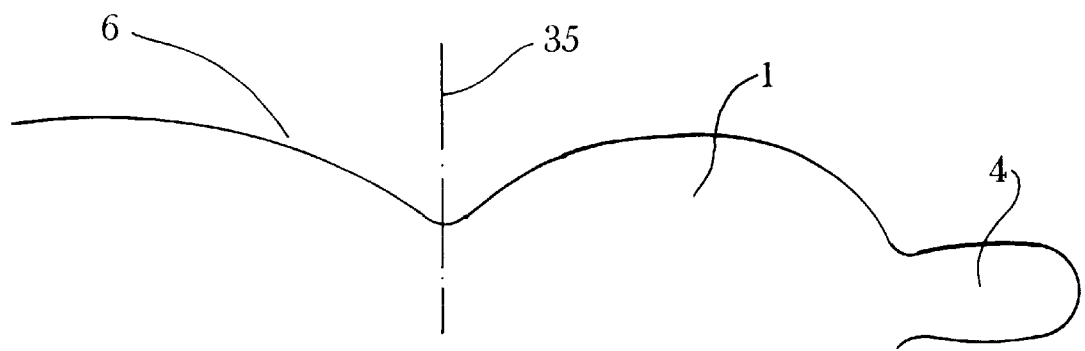
FIG. 11a shows a schematic representation of an asymmetrical annular groove (34) in the valley (6) of a shaped plunger tool (1)
Figure 11B:
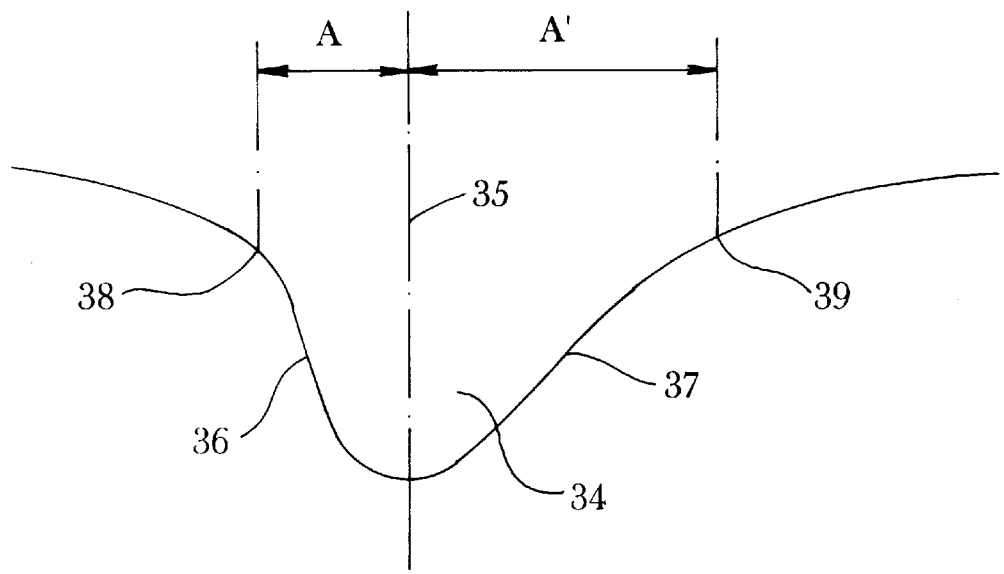
FIG. 11b shows an enlarged annular groove (34).

FIG. 11a shows the upper shaped section of a plunger tool 1, representing half of said section. In narrowing 6, a symmetrical annular groove 34 is located at the deepest point, which groove was ground with the diamond grinding tip 32 according to the invention. The asymmetry of said annular groove 34 relates to the imaginary center axis 35, which extends vertically on the longitudinal axis of plunger tool 1. Characteristic of said asymmetrical annular groove 34 are the different pitches of the walls 36, 37 (see FIG. 11b) limiting the annular groove. It is important in this connection that wall 36, which in this drawing is seen to the left of center axis 35, is steeper than wall 37 shown to the right of center axis 35. The ratio of spacings A, A' of annular groove edges 38, 39 relative to each other should be A;A'=1:2. This asymmetry in the cross section of annular groove 34 is important for the flow behavior of the elastic material (latex) when emerging from the latex bath. Air inclusions or other uneven spots in the material of the prophylactic to be produced are avoided in this way.

With the grinding process of the invention for producing plunger tools, in particular the annular grooves 17, 18, 34 on the surface of plunger tool 1, it is possible to manufacture clean and precise grindings in the surface, which assures clean spreading of the elastic material, as opposed to other production methods for producing annular grooves, for example in the chemical way by etching.

What is claimed is:

1. A plunger tool for producing a prophylactic comprising:
   (a) an oblong cylindrical section;
   (b) an S-shaped section having a radius of curvature and a narrowing formed by an upper and a lower blunt cone abutting each other with their covering surfaces, the narrowing having a constant gradient extending in the longitudinal direction of the surface of the plunger tool to a point in which the diameter of the S-shaped section is at its narrowest;
   (c) a reservoir section adjoining said S-shaped section, said reservoir section having portions forming an inlet and a closed end in the prophylactic; wherein:
   the diameter of the plunger tool at the narrowest point of the narrowing amounts to between 15 and 25 mm;
   the radius of curvature at the narrowest point of the narrowing amounts to between 17 and 20;
   the upper blunt cone is open toward the reservoir section and has an opening angle amounting to 50 degrees;
   the lower blunt cone has an opening angle amounting to 40 degrees;
   a point of transition exists between the cylindrical section and the narrowing in the S-shaped section and the radius of curvature at the point of transition from the cylindrical section to the narrowing in the S-shaped section is convex and greater than 25 mm;
   the total length from the narrowing to the inlet portion of the reservoir section is between 45 mm and 65 mm; and
   the largest diameter of the S-shaped section between the narrowing and the inlet portion of the reservoir section amounts to between 33 and 35 mm.

2. A plunger tool according to claim 1 wherein at least one annular groove is arranged within the area where the diameter of the narrowing is the narrowest.

3. A plunger tool according to claim 2, comprising more than one annular groove, the annular grooves being spaced apart from each other and the spacing between the annular grooves amounting to about 1.5 mm.

4. A plunger tool for producing a prophylactic comprising:
   (a) an oblong cylindrical section;
   (b) an S-shaped section having a radius of curvature and a narrowing formed by two blunt cones abutting each other with their covering surfaces, the narrowing having a constant gradient extending in the longitudinal direction of the surface of the plunger tool; and
   (c) a club-like reservoir section adjoining said S-shaped section, said reservoir section having a portion forming a closed end in the prophylactic; wherein:
   (d) an area of transition exists between the reservoir section and the S-shaped section and the radius of curvature in the area of transition between the reservoir section and the S-shaped section is concave and greater than or equal to 12 mm; and
   a point of reversal exists in the S-shaped curve in the S-shaped section between the area where the diameter of the S-shaped section is the greatest and the area of transition between the S-section and the reservoir section and a tangent at the point of reversal of the S-shaped curve in the S-shaped section between the area where the diameter of the S-shaped section is the greatest and the area of transition between the S-section and the reservoir section encloses an angle relative to the center longitudinal axis of the plunger tool between 40 degrees and 75 degrees.

5. A plunger tool according to claim 4, wherein the reservoir section has an area which forms an inlet in the prophylactic, said inlet-forming area of the reservoir section having an upper area and a lower area, the diameter of the inlet-forming area of the reservoir section being between 6 mm and 11 mm in the lower area, and the maximum diameter of the reservoir section amounting to between 11 and 14 mm.

6. A plunger tool according to claim 4, wherein the convex radius of curvature within the closed end portion of the reservoir section comes to about 6 mm.

7. A plunger tool according to claim 4, wherein elastic material is to be applied to said tool in producing the prophylactic and the course of the curve of the club-like reservoir section promotes uniform distribution of the elastic material to be applied.

8. A process for producing a prophylactic, said prophylactic consisting of
   (a) an oblong cylindrical section;
   (b) an S-shaped section; and
   (c) a reservoir section adjoining said s-shaped section, said reservoir having a closed end; and
   (d) a shaped section made of thin-walled elastic material, said elastic material being externally applied to a plunger tool corresponding to the shape of the prophylactic;
said process comprising:
   (e) immersing the plunger tool in two immersion operations in the elastic material to be applied and rotating the tool around its longitudinal axis in a position inclined relative to the surface of the elastic material; and
   (f) stripping off the finished prophylactic with brushes rotating in opposite directions and at least one water jet acting on the plunger tool.

9. A process according to claim 8 wherein a rolling ring is used during the stripping operation and at least one water jet is directed in such a way that the jet directly acts on the plunger tool behind the rolling ring during the stripping operation.

10. A process for producing a prophylactic having a surface and a plurality of annular grooves on said surface, said process involving the use of a plunger tool having a surface wherein annular grooves for forming the annular grooves on the surface of the prophylactic are ground into the surface of the plunger tool with the help of at least one wheel-like, finely granular diamond grinding tip having a front part, the angle of such tip being between 60 degrees and 120 degrees, and the front part of the diamond grinding tip being blunt.

11. A process according to claim 10, wherein the height of the blunt part is between 0.2 and 0.6 mm.

12. A process according to claim 10, wherein five diamond tips are arranged on a grinding wheel.

13. A process according to claim 10, wherein the annular grooves in the surface of the plunger tool are produced with the blunt diamond grinding tip, said grooves in said plunger tool not having any sharp edges and having an opening of between 0.2 and 0.6 mm.

14. A process according to claim 10, wherein the annular grooves in the surface of the plunger tool are shaped symmetrically relative to the center axis of the tool.

15. A process according to claim 10, wherein the annular grooves in the surface of the plunger tool have walls shaped asymmetrically relative to the center axis so that the wall of the annular groove to the left of the axis is steeper than the wall to the right of the axis.

16. A process according to claim 10, wherein the annular groove in the plunger tool has a distance A from the center axis to one edge of the annular groove and a distance A' from the center axis to the other edge of the annular groove, and the ratio of A:A' is approximately 1:2.

* * * * *